United States Patent
Noda et al.

(10) Patent No.: US 7,258,442 B2
(45) Date of Patent: Aug. 21, 2007

(54) EYE FUNDUS PHOTOGRAPHING SYSTEM

(76) Inventors: Toru Noda, 1-3 Fujisaki 1-chome, Kawasaki-ku, Kawasaki-shi, Kanagawa 210-0804 (JP); Yoshio Okazaki, c/o Kabushiki Kaisha Topcon, 75-1 Hasunuma-cho, Itabashi-ku, Tokyo 174-8580 (JP); Hidetaka Aeba, c/o Kabushiki Kaisha Topcon, 75-1 Hasunuma-cho, Itabashi-ku, Tokyo 174-8580 (JP); Yasufumi Fukuma, c/o Kabushiki Kaisha Topcon, 75-1 Hasunuma-cho, Itabashi-ku, Tokyo 174-8580 (JP)

(*) Notice: Subject to any disclaimer, the term of this patent is extended or adjusted under 35 U.S.C. 154(b) by 243 days.

(21) Appl. No.: 11/154,670

(22) Filed: Jun. 17, 2005

(65) Prior Publication Data
US 2006/0139572 A1    Jun. 29, 2006

(30) Foreign Application Priority Data
Jun. 25, 2004    (JP)    ............................. 2004-188752

(51) Int. Cl.
*A61B 3/14*    (2006.01)

(52) U.S. Cl. ............................. 351/206; 351/205; 351/213; 351/221

(58) Field of Classification Search ................ 351/205, 351/206, 208–211, 213–215, 221
See application file for complete search history.

(56) References Cited

U.S. PATENT DOCUMENTS

2005/0237486 A1*    10/2005    Su et al. .................... 351/206

FOREIGN PATENT DOCUMENTS

| JP | 05-15499 | 1/1993 |
| JP | 09-276227 | 10/1997 |
| JP | 2000-316812 | 11/2000 |

* cited by examiner

*Primary Examiner*—Huy Mai
(74) *Attorney, Agent, or Firm*—Edwards Angell Palmer & Dodge LLP

(57) ABSTRACT

An eye fundus photographing system, wherein a three-dimensional moving picture is photographed and displayed in eye fundus of infrared fluorescent photographing. The photographing system includes an exciter filter for transmitting a specific wavelength region of the illumination light emitted from the light source, an illumination optical system for irradiating the fundus with the illumination light transmitted from the exciter filter, left and right objective lenses for extracting the infrared fluorescent light emitted by an ICG of the eye fundus as a left and right photographing light, a photographing optical system including a barrier filter for transmitting the predetermined infrared wavelength region of the left and right photographic light, infrared TV cameras for photographing this wavelength region with a predetermined frame rate, a synchronizing cable for synchronizing each frame and a displayed three-dimensional moving image obtained by combining a left and right photographic image by the infrared TV camera.

11 Claims, 5 Drawing Sheets

EYE FUNDUS PHOTOGRAPHING SYSTEM

BACKGROUND OF THE INVENTION

1. Field of the Invention

The present invention relates to an eye fundus photographing system for photographing a fundus of an eye to be examined, and more particularly to a fluorescent photographing technique for suitably diagnosing a vascular lesion of a retina or a choroid.

2. Description of the Related Art

Eye fundus examination undertakes an important role in an ophthalmologic field and has been conducted mainly using a slit lamp microscope (slit lamp) or a fundus camera. The eye fundus examination using the slit lamp is performed through a front lens located immediately before an eye to be examined to cancel refracting power of a crystalline lens or the like. For the eye fundus examination using the fundus camera, fluorescent photographing for photographing a state of an eye fundus blood vessel in detail has been widely used in addition to normal photographing methods such as monochrome photographing and color photographing.

In the fluorescent photographing of the eye fundus using the fundus camera, a person to be examined is subjected to intravenous injection with a fluorescent dye material (fluorescent agent) and fluorescence radiated from a fluorescent dye material is photographed. Visible fluorescent photographing in a visible light wavelength region or infrared fluorescent photographing in an infrared light wavelength region has been conducted according to a wavelength region of the radiated fluorescence. Generally, fluorescein (FAG) is used as the fluorescent dye material for the visible fluorescent photographing. In addition, indocyanine green (ICG) pigment is used for the infrared fluorescent photographing. In the infrared fluorescent photographing, each of excitation light resulting from the ICG and fluorescence is near-infrared light, so it is suitable to detect a lesion under preretinal hemorrhages or subretinal hemorrhages, detect a lesion of a choroid coat, or understand a state of a new blood vessel. Therefore, the infrared fluorescent photographing has been widely used.

According to JP 2000-316812 A (claim 1 and paragraph [0014]), an example of a fundus camera capable of performing the infrared fluorescent photographing has been disclosed. In order to reduce a cost while illumination efficiency is maintained, the fundus camera described in this document includes an infrared laser and a xenon lamp which serve as fluorescent photographing light sources for the fundus of an eye to be examined. In the early phase of fluorescence, the fundus of the eye to be examined is illuminated with mainly light from the infrared laser to perform moving picture photographing. In the late phase of the fluorescence, the fundus of the eye to be examined is illuminated with mainly light from the xenon lamp to perform still image photographing. The fundus camera described in this document can perform color photographing, visible fluorescent photographing, and infrared fluorescent photographing by switching among photographing modes.

A fundus camera capable of photographing a three-dimensional image of the eye fundus has been proposed. For example, according to an eye fundus image described in JP 05-015499A (paragraphs [0016] to [0018] and FIG. 2), eye fundus reflection light passing through an objective lens is divided into right and left light beams. Those light beams are imaged on a film by separate optical systems to produce a three-dimensional-image.

A parallel shift method is used as a general method of producing a three-dimensional image in the fundus camera. According to this method, a photographing region of the eye fundus is minutely shifted in parallel to obtain two images. The obtained images are synthesized with each other to produce the three-dimensional image. However, in the parallel shift method, the two images used to produce the three-dimensional image are not obtained by simultaneous photographing. Therefore, even when a photographing interval minimizes, it is impossible to obtain an accurate three-dimensional image.

According to JP 09-276227 A (claim 1), an example of a slit lamp used for an eye fundus examination has been disclosed. The slit lamp described in this document includes a main body, a pillar having a chin rest portion for supporting a chin of a person to be examined, an arm pivotally attached to the pillar, a fixation unit pivotably provided substantially in the end portion of the arm, and a lens holder that holds a front lens for observing the eye fundus of the person to be examined. The lens holder is detachably provided in the pivot center of the fixation unit.

A recent establishment of an infrared fluorescent photographing method improves pathologic resolutions of vascular lesions of a retina and a choroid coat. When the pathology is to be understood in more detail, it may be necessary to apply a new photographing mode which cannot be performed by a conventional fundus camera or a conventional slit lamp. For example, if a three-dimensional moving picture image of the eye fundus can be obtained by the infrared fluorescent photographing to observe the three-dimensional moving picture image in real time, a state of a blood vessel may be recognized in extreme detail.

SUMMARY OF THE INVENTION

The present invention has been made in view of the above-mentioned circumstances. Therefore, an object of the present invention is to provide an eye fundus photographing system that can obtain and display a three-dimensional moving picture image by infrared fluorescent photographing of an eye fundus.

To solve the object, a first aspect of the invention relates to an eye fundus photographing system, including: an illumination optical system that includes a light source for emitting illumination light and an exciter filter for transmitting a specific wavelength region of the illumination light emitted from the light source and that emits the illumination light passing through the exciter filter to a fundus of an eye to be examined; a photographing optical system including right and left objective lenses for taking right and left photographing light beams based on infrared fluorescence radiated from an infrared fluorescent dye material excited by the illumination light emitted to the fundus and a barrier filter for transmitting a predetermined infrared wavelength region of each of the right and left photographing light beams; right and left photographing means for obtaining photographed images of respective frames based on the right and left photographing light beams passing through the barrier filter; synchronization means for synchronizing the respective frames between the right and left photographing means; and three-dimensional image displaying means for displaying a three-dimensional moving picture image based on the photographed images of the synchronized respective frames which are obtained by the right and left photographing means.

Further, to solve the object, a second aspect of the invention relates to an eye fundus photographing system according to the first aspect, further including a longitudinal magnification increasing lens for increasing longitudinal magnification of each of the photographed images obtained by the right and left photographing means.

Further, to solve the object, a third aspect of the invention relates to an eye fundus photographing system according to the first or second aspect, further including: converting means f or converting the right and left photographed images of the respective frames which are obtained by the right and left photographing means into two different color signals of RGB signals; and display control means for outputting the two different color signals of each of the frames to the three-dimensional image displaying means in frame order to display the three-dimensional moving picture image.

Further, to solve the object, a fourth aspect of the invention relates to an eye fundus photographing system according to the first or second aspect, further including: converting means for converting the right and left photographed images of the respective frames which are obtained by the right and left photographing means into two different color signals of RGB signals and converting the two different color signals of the respective frames into a composite signal by synthesization; image recording means for recording the converted composite signal of each of the frames; and display control means for outputting the recorded composite signal of each of the frames to the three-dimensional image displaying means in frame order to display the three-dimensional moving picture image.

Further, to solve the object, a fifth aspect of the invention relates to an eye fundus photographing system according to any one of first to fourth aspects, in which the synchronization means includes: a synchronization signal generating circuit that is provided in one of the right and left photographing means and that generates a synchronization signal in synchronization with each of the frames of the one of the right and left photographing means; a cable for connecting between the right and left photographing means and transmitting the synchronization signal generated by the synchronization signal generating circuit to the other of the right and left photographing means; and a synchronous control circuit that is provided in the other of the right and left photographing means and that controls each of the frames of the other of the right and left photographing means in response to the synchronization signal transmitted through the cable.

Further, to solve the object, a sixth aspect of the invention relates to an eye fundus photographing system according to any one of the first to fifth aspects, further including: time measuring means for staring time measurement in response to start of illumination of the fundus with the illumination light from the light source; and control means for stopping the illumination when a time measured by the time measuring means reaches a preset time.

Further, to solve the object, a seventh aspect of the invention relates to an eye fundus photographing system according to any one of the first to sixth aspects, in which the illumination optical system further includes light shielding means for blocking the illumination light emitted from the light source, and the eye fundus photographing system further includes: light shielding drive means for inserting and retreating the light shielding means into and from an optical path of the illumination optical system; time measuring means for staring time measurement in response to start of illumination of the fundus with the illumination light from the light source; and control means for controlling the light shielding drive means to insert the light shielding means into the optical path when a time measured by the time measuring means reaches a preset time.

Further, to solve the object, an eighth aspect of the invention relates to an eye fundus photographing system according to any one of the first to seventh aspects, in which the illumination optical system further includes an observation light source for emitting illumination light for fundus observation, and the eye fundus photographing system further includes: an observation optical system that uses the right and left objective lenses common to the photographing optical system and respectively guides right and left observation light beams extracted from fundus reflection light of the illumination light for fundus observation to right and left eyepieces by the right and left objective lenses; and optical path changing means for guiding the right and left photographing light beams taken by the right and left objective lenses to optical paths of the photographing optical system and guiding the right and left observation light beams to optical paths of the observation optical system.

Further, to solve the object, a ninth aspect of the invention relates to an eye fundus photographing system according to the eighth aspect, in which the optical path changing means includes a total reflection mirror for totally reflecting light having an infrared wavelength region, of each of the right and left photographing light beams passing through the barrier filter to guide the totally reflected light to an optical path of the photographing optical system.

Further, to solve the object, a tenth aspect of the invention relates to an eye fundus photographing system according to the eighth aspect, in which the optical path changing means includes a dichroic mirror for reflecting light having an infrared wavelength region, of each of the right and left photographing light beams passing through the barrier filter to guide the reflected light to the optical path of the photographing optical system and transmitting light having a visible wavelength region to guide the transmitted light to the optical path of the observation optical system.

Further, to solve the object, an eleventh aspect of the invention relates to an eye fundus photographing system according to the eighth aspect, further including laser irradiating means for irradiating the fundus with laser light for photocoagulation treatment along an optical axis of the illumination optical system.

According to the eye fundus photographing system of the present invention, the right and left photographing light beams are taken based on the infrared fluorescence radiated from the infrared fluorescent dye material excited by the illumination light. Light having the predetermined infrared wavelength region is extracted from each of the right and left photographing light beams. Photographing using the right and left photographing light beams is performed by the right and left photographing means in which the respective frames are synchronized with each other. The three-dimensional moving picture image formed based on the right and left photographed images is displayed on the three-dimensional displaying means. Therefore, according to the eye fundus photographing system of the present invention, the three-dimensional moving picture image can be obtained and displayed by the infrared fluorescent photographing of the eye fundus. As compared with the conventional three-dimensional image produced by the parallel shift method, the eye fundus photographing system of the present invention forms the three-dimensional moving picture image from the right and left photographed images based on the simultaneously obtained right and left photographing light beams.

In particular, according to the eye fundus photographing system in the second aspect, the lens for increasing the longitudinal magnification of the photographed image is provided, so a three-dimensional moving picture image having an increased spacial effect can be obtained. Therefore, it is possible to grasp states of a retinal blood vessel and a choroidal blood vessel in detail.

According to the eye fundus photographing system in the eighth aspect, a structure for infrared fluorescent photographing of the eye fundus can be provided in an ophthalmic apparatus having an observation optical system. When a slit lamp is used as such an ophthalmic apparatus, the infrared fluorescent photographing can be conducted in addition to observation and photographing using a normal slit lamp.

According to the eye fundus photographing system in the eleventh aspect, laser irradiation can be performed while a three-dimensional moving picture image indicating a detailed lesion portion of an eye fundus blood vessel which is obtained by the infrared fluorescent photographing is observed. Therefore, it is possible to easily perform high accuracy photocoagulation treatment.

DETAILED DESCRIPTION OF THE PREFERRED EMBODIMENT

Hereinafter, an example of an eye fundus photographing system according to a preferred embodiment of the present invention will be described in detail with reference to the drawings. The following detailed eye fundus photographing system is composed of mainly slit lamp. The slit lamp has not only a function as a conventional slit lamp but also an eye fundus photographing function according to the present invention.

[Structure of Eye Fundus Photographing System]

[Schematic Structure]

Figure 1:
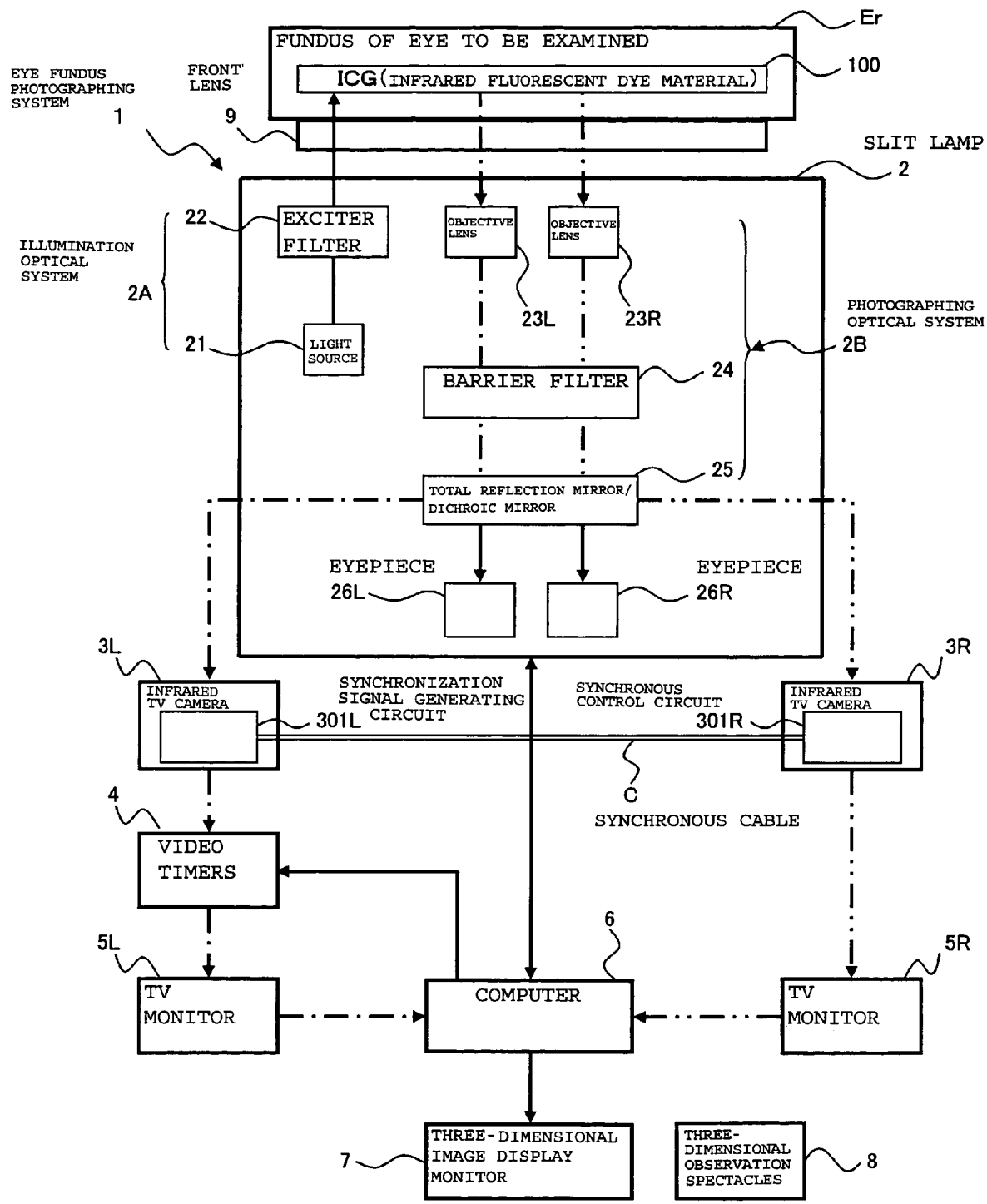
FIG. 1 is a block diagram showing an example of a schematic structure of an eye fundus photographing system according to an embodiment of the present invention.

First, an example of a schematic structure of the eye fundus photographing system according to this embodiment will be described. FIG. 1 shows a schematic structure of an entire eye fundus photographing system 1 according to this embodiment. The eye fundus photographing system 1 is an apparatus for performing infrared fluorescent photographing on a fundus Er of an eye to be examined and has a feature in which a three-dimensional moving picture image of the fundus Er can be obtained.

When photographing is performed using the eye fundus photographing system 1, a front lens 9 having refracting power for imaging illumination light on the fundus Er of the eye to be examined and increasing longitudinal magnification of a photographed image (magnification in an optical direction of photographing light) is disposed in an anterior segment of the eye to be examined. Note that, the front lens 9 composes a longitudinal magnification increasing lens according to the present invention.

A contact type front lens (contact lens) or a non-contact type front lens can be used as the front lens 9. When the contact type front lens is used, the position of the front lens is fixed. Therefore, there is an advantage that a variation in the photographed image does not occur. In addition, according to the contact type front lens, there is a merit that an eye fundus image can be obtained over a wide range. Lenses having various magnifications can be selectively used, so the number of choices of longitudinal magnifications provided to the photographed image increases. In particular, when the front lens 9 having large longitudinal magnification is used, a spacial effect of the photographed image can be increased. On the other hand, the non-contact type front lens reduces a burden on a person to be examined and has an advantage in the health aspect. Here, for example, applications to laser treatment as described later is taken into account and examination accuracy is to be improved by using the contact type front lens 9.

The eye fundus photographing system 1 includes a slit lamp 2 for photographing and observing the fundus Er of the eye to be examined, left and right infrared TV cameras 3L and 3R which are connected with the slit lamp 2, and a synchronous cable C composing a cable in the present invention, for connecting the infrared TV cameras 3L and 3R with each other. The eye fundus photographing system 1 further includes a video timer 4 connected with the left infrared TV camera 3L, a TV monitor 5L connected with the video timer 4, a TV monitor 5R connected with the right infrared TV camera 3R, a computer 6 connected with the TV monitors 5L and 5R, and a three-dimensional image display monitor 7 connected with the computer 6. Note that, a three-dimensional observation spectacles 8 has, for example, a red plate for the right eye and a green plate for the left eye. In order to visually recognize an image displayed on the three-dimensional image display monitor 7 as a three-dimensional image, an examiner puts on the three-dimensional observation spectacles 8.

The slit lamp 2 has an illumination optical system 2A and a photographing optical system 2B. The illumination optical system 2A includes various optical elements for irradiating the fundus Er with illumination light for exciting ICG (indocyanine green; infrared fluorescent dye material) F injected into the person to be examined by intravenous injection. The photographing optical system 2B includes various optical elements for photographing infrared fluorescence emitted by exciting an ICG 100 with the illumination light. As in the case of a normal slit lamp, an optical axis of the illumination optical system 2A is not the same as that of the photographing optical system 2B and these optical systems are disposed to form a predetermined angle with the optical axis each other.

The illumination optical system 2A specifically includes a light source 21 for emitting the illumination light and an exciter filter 22 for transmitting light having a specific wavelength region, of the illumination light emitted from the light source 21, that is, light which is used to excite the ICG 100 and has a wavelength region close to 780 nm.

The photographing optical system 2B specifically includes left and right objective lenses 23L and 23R, a barrier filter 24, and a total reflection mirror/dichroic mirror 25. The objective lenses 23L and 23R are used for taking the infrared fluorescence emitted from the ICG 100 as left and right photographing light beams. The barrier filter 24 transmits light having a predetermined infrared wavelength region, of each of the taken left and right photographing light beams, that is, light which is emitted from the ICG 100 and has a wavelength region close to 805 nm which is a wavelength region of the infrared fluorescence. The total reflection mirror/dichroic mirror 25 is used to guide the left and light photographing light beams passing through the barrier filter 24 to the infrared TV cameras 3L and 3R.

The total reflection mirror/dichroic mirror 25 is used by switching according to, for example, an examination aspect. The total reflection mirror 25 guides the left and right photographing light beams passing through the barrier filter 24 to the infrared TV cameras 3L and 3R by total reflection. The dichroic mirror 25 reflects infrared light and transmits visible light. When the eye to be examined is observed or when each of the right and left photographing light beams includes a wavelength of a visible region, the dichroic mirror 25 transmits the visible light (visible component) to guide the visible light to the left and right eyepieces 26L and 26R. Note that the right and left photographing light beams each having the infrared wavelength region which are reflected on the total reflection mirror/dichroic mirror 25 are guided to the infrared TV cameras 3L and 3R through TV relay lens systems as described later. Switching between the total reflection mirror 25 and the dichroic mirror 25 may be performed manually or may be performed by a drive device such as a solenoid. When the drive device is applied, automatic switching may be performed according to a selected photographing mode as described later. The total reflection mirror/dichroic mirror 25 composes an optical path switching means according to the present invention.

Each of the infrared TV cameras 3L and 3R is a high-sensitive infrared TV camera for moving-picture photographing which is used to photograph the light having the infrared wavelength region at a predetermined frame rate. The infrared TV camera 3L and 3R are connected with each other through the synchronous cable C. The left infrared TV camera 3L includes a synchronization signal generating circuit 301L for generating a synchronization signal that synchronizes with each frame. The right infrared TV camera 3R includes a synchronous control circuit 301R for controlling each frame in response to the synchronization signal transmitted from the left infrared TV camera 3L through the synchronous cable C. Therefore, the left and right infrared TV cameras 3L and 3R are controlled so as to synchronize photographing timings of respective frames and to perform photographing at the same frame rate. Note that, the infrared TV cameras 3L and 3R compose left and right photographing means in the present invention. The synchronization signal generating circuit 301L, the synchronous control circuit 301R, and the synchronous cable C compose a synchronization means in the present invention.

In this embodiment, the structure including the right and left separate photographing means is employed. It is also possible that a single infrared TV camera composes the right and left photographing means. For example, a single infrared TV camera having a large light receiving surface is prepared. When the left photographing light beam is received on a part of a region of the light receiving surface and the right photographing light beam is received on the remaining region, the right and left photographing means can be realized by the single infrared TV camera.

The video timer 4 starts time measurement at a predetermined timing to perform processing for adding a measured time to the image photographed by the left infrared TV camera 3L. To explain in more detail, the video timer 4 is a device for adding measured time data to a video signal sent from the infrared TV camera 3L.

The TV monitors 5L and 5R are monitor devices for separately displaying the left and right photographed images obtained by the infrared TV cameras 3L and 3R. The TV monitors 5L and 5R separately display as monochrome images the photographed images related to an infrared wavelength region, which are obtained by the infrared TV cameras 3L and 3R. The measured time added by the video timer 4 is imposed on the photographed image displayed on the left TV monitor 5L.

In this embodiment, the structure including the right and left separate TV monitors is applied. It is also possible to display both the right and left photographed images on a single TV monitor at the same time. For example, two display regions are set on a screen of the single TV monitor. Therefore, it is possible to display the photographed image obtained by the left infrared TV camera 3L on one of the set display regions and display the photographed image obtained by the right infrared TV camera 3R on the other. In this case, it is preferable to use a TV monitor having a relatively large screen.

Although the detail of the computer 6 will be described later, the computer 6 converts one of monochrome video signals sent from the TV monitors L and 5R into a red signal (R signal) of RGB signals, converts the other into a green signal (G signal) thereof, and records the R signal and the G signal. In addition, the computer 6 synthesizes the R signal and the G signal with each other and outputs a synthesized signal to the three-dimensional image display monitor 7.

The three-dimensional image display monitor 7 is a three-dimensional image display means in the present invention and displays a three-dimensional image based on the synthesized signal (R signal and G signal) outputted from the computer 6. For example, a three-dimensional viewer device of various types for displaying an image based on such as a composite signal, RGB signals, or a monochrome signal, a monitor device for displaying an image based on RGB signals, monochrome signal, or the like such as a CRT display or an LCD can be suitably used as the three-dimensional image display monitor 7.

[Structure of Optical System of Slit Lamp]

Figure 2:
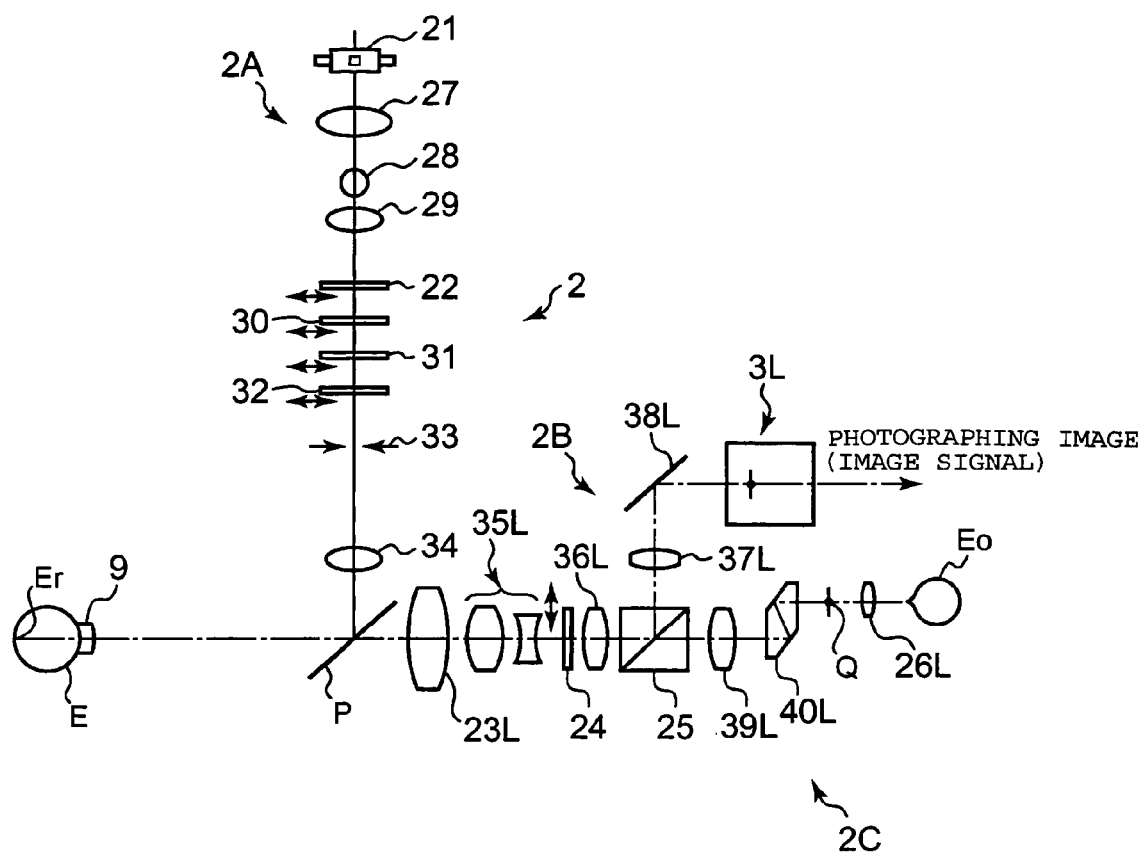
FIG. 2 is a schematic view showing an example of an optical structure of a slit lamp of the eye fundus photographing system according to the embodiment of the present invention.

Subsequently, an example of a schematic structure of an optical system of the slit lamp 2 will be described with further reference to FIG. 2.

The slit lamp 2 includes an observation optical system 2C for performing cornea cross sectional image observation and eye fundus observation on an eye to be examined E as a-normal slit lamp use mode in addition to the illumination optical system 2A and the photographing optical system 2B which are described above. Note that, FIG. 2 shows an optical structure for guiding the left photographing light to the left infrared TV camera 3L in the photographing optical system 2B and an optical structure for guiding observation light to a left eye Eo of an examiner in the observation optical system 2C. An optical structure for guiding the right photographing light to the right infrared TV camera 3R and an optical structure for guiding the observation light to the right eye of the examiner are identical to those shown in FIG. 2.

(Illumination Optical System)

The illumination optical system 2A includes the light source 21, a condensing lens 27, a stroboscopic light source 28, a condensing lens 29, the exciter filter 22, a heat prevention filter 30, a light reducing filter 31, a light shielding filter 32, a slit forming means 33, and a condensing lens 34. The exciter filter 22, the heat prevention filter 30, the light reducing filter 31, and the light shielding filter 32 are constructed to be insertable into and removable from the optical path of the illumination optical system 2A (drive modes will be described later in detail).

The light source 21 composes a light source and an observation light source in the present invention and is composed of a halogen lamp or the like which emits light in response to power supplied from a power source device which is not shown. The condensing lens 27 is a lens for condensing illumination light emitted from the light source 21.

The stroboscopic light source 28 is composed of a xenon lamp or the like which emits stroboscopic light in response to power supplied from a power source device which is not shown. The condensing lens 29 is a lens for condensing illumination light emitted from the stroboscopic light source 28 (and the light source 21).

The heat prevention filter 30 is a filter for cutting off a predetermined infrared wavelength region of the illumination light emitted from the light source 21 or the stroboscopic light source 28 and used to provide a heat prevention effect to the eye to be examined E.

The light reducing filter 31 is a filter for reducing the amount of illumination light emitted from the light source 21 or the stroboscopic light source 28 in order to perform exposure adjustment on the photographed image and the like. In this embodiment, the light reducing filter 31 is provided in the illumination optical system 2A. The light reducing filter 31 may be provided in only the photographing optical system 2B or each of the illumination optical system 2A and the photographing optical system 2B. When the latter structure in which the light reducing filter 31 is provided in each of the illumination optical system 2A and the photographing optical system 2B is applied, any light reducing filter may be selectively used or both may be simultaneously used.

The light shielding filter 32 composes a light shielding means in the present invention and is a filter for blocking the illumination light emitted from the light source 21 or the stroboscopic light source 28.

The slit forming means 33 is used when the slit lamp 2 is used as a normal slit lamp (for observation and photographing on a cornea cross sectional image, an eye fundus, and the like). The slit forming means 33 is composed of, for example, a pair of slit blades fixed to a case housing the illumination optical system 2A and transmits only a part of light emitted from the light source 21 or the stroboscopic light source 28 to produce slit light. Hereinafter, assume that the slit forming means 33 is identical to a slit formed thereby (the slit is indicated by reference numeral 33).

The pair of slit blades of the slit forming means 33 are driven by a drive device described later such that an interval therebetween (slit width) can be changed. When the slit width is maximized, the optical path of the illumination optical system 2A is opened (in other words, the eye to be examined E is irradiated with the illumination light without any illumination light being blocked). Here, the illumination light of the infrared wavelength region has a long frequency, so the illumination light is not reflected on the cornea. Therefore, this case is different from the case using the light of the visible wavelength region and it is unnecessary to use the illumination light as the slit light. When the illumination light is not used as the slit light, the amount of illumination light becomes larger, so that a bright photographed image can be obtained.

Assume that the illumination light with which the eye to be examined E is irradiated by the illumination optical system 2A is overlapped partly with the photographing light incident on the photographing optical system 2B to cause interference. In such a case, it is preferable to set a slit width in which the overlapping does not occur without maximizing a slit width at the time of the infrared fluorescent photographing.

The condensing lens 34 has a function for condensing the illumination light passing through the slit 33. The illumination light condensed by the condensing lens 34 is reflected on a prism P. The eye to be examined E is irradiated with the reflected illumination light through the front lens 9.

(Photographing Optical System)

The (left) photographing optical system 2B of the slit lamp 2 includes the objective lens 23L, a variable lens system 35L, the barrier filter 24, a condensing lens 36L, the total reflection mirror/dichroic mirror 25, a condensing lens 37L, and a reflecting mirror 38L. The barrier filter 24 is constructed to be insertable into and removable from the optical path of the left photographing light.

The objective lens 23L is a lens for taking left photographing light from eye fundus reflection light of the illumination light or the fluorescence caused by excitation which passes through the front lens 9 and the prism P. The variable lens system 35L is a lens group shifted in an optical path direction of the photographing light by a drive device (not shown) to change the magnification of the photographed image. A variation in magnification of the photographed image which is caused by the variable lens system 35L affects lateral magnification (magnification in a direction orthogonal to the optical direction of the photographing light). Each of the condensing lenses 36L and 37L is a lens for condensing the photographing light. The reflecting mirror 38L is a mirror for reflecting the photographing light condensed by the condensing lens 37L to the infrared TV camera 3L. Although not shown, the photographing light reflected on the total reflection mirror/dichroic mirror 25 is relayed to the infrared TV camera 3L by a TV relay lens system including the condensing lens 37L and the reflecting mirror 38L.

(Observation Optical System)

The (left) observation optical system 2C of the slit lamp 2 includes the objective lens 23L, the variable lens system 35L, the barrier filter 24, the condensing lens 36L, the total reflection mirror/dichroic mirror 25, a relay lens 39L, a prism 40L, and the eyepiece 26L.

The objective lens 23L is used to take left observation light from the eye fundus reflection light of the illumination light or the fluorescence caused by excitation which passes through the front lens 9 and the prism P. The variable lens system 35L is shifted in an optical path direction of the observation light by the drive device (not shown) to change the magnification of an observed image. The barrier filter 24 is constructed to be insertable into and removable from the optical path of the observation light. The observation light condensed by the condensing lens 36L passes through the dichroic mirror 25 and is relayed by the relay lens 39L. A traveling direction of the observation light is shifted in parallel by the prism 40L. Then, the observation light is imaged on an imaging point Q as a cornea cross sectional image or an eye fundus image. The examiner observes the image enlarged by the eyepiece 26L.

Hereinafter, each of optical elements included in the right photographing optical system 2B and the right observation optical system 2C is indicated by adding "R" to the same numeral ("35" in this embodiment) as that of an optical element of the left optical system as in the case of, for example, the "variable lens system 35R".

[Structure of Control System of Eye Fundus System]

Figure 3:
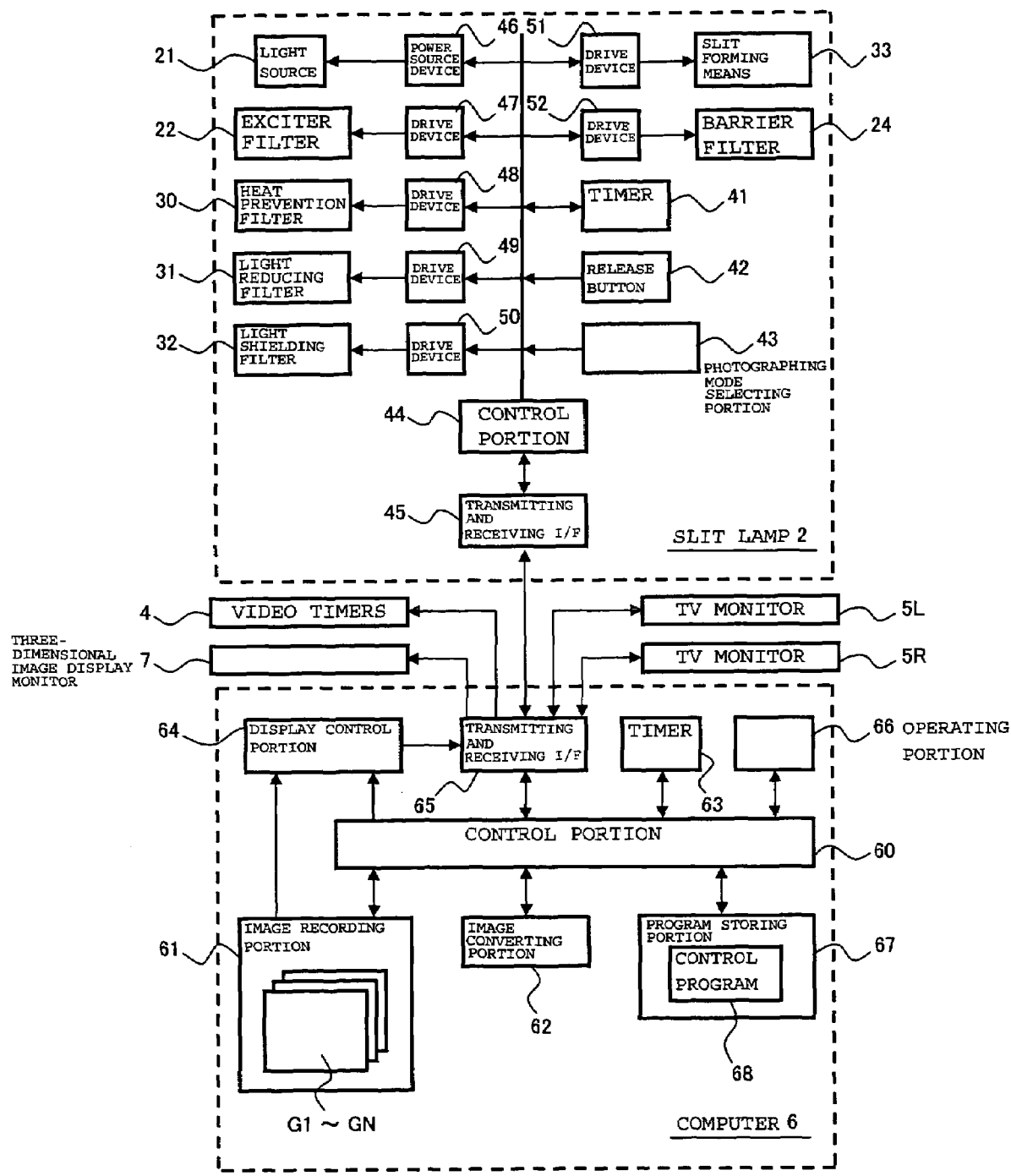
FIG. 3 is a block diagram showing an example of a structure of a control system of the eye fundus photographing system according to the embodiment of the present invention.

Next, a structural example of a control system of the eye fundus photographing system 1 according to this embodiment will be described with further reference to a block diagram shown in FIG. 3. FIG. 3 shows a control system of the slit lamp 2 and a control system of the computer 6 in the eye fundus photographing system 1.

(Control System of Slit Lamp)

First, the control system of the slit lamp 2 will be described. The slit lamp 2 includes a timer 41, a release button 42 which is pressed down, for example, when the infrared fluorescent photographing starts, and a photographing mode selecting portion 43 operated at the time of various-photographing-mode selection setting.

The photographing mode selecting portion 43 is composed of, for example, a control panel in which a selection button is provided for each photographing mode or a touch panel type liquid crystal monitor in which a soft key is provided for each photographing mode. The examiner operates a selection button or a soft key corresponding to a desirable photographing mode to select the photographing mode. The photographing mode set by the photographing mode selecting portion 43 includes an infrared fluorescent photographing mode featured in the present invention and a color photographing mode performed by a normal slit lamp.

A filter operating portion operated when the exciter filter 22 or the barrier filter 24 is to be inserted into or retreated from the optical path may be provided instead of the photographing mode selecting portion 43 or in addition thereto. The filter operating portion can include an exciter filter operating button for inserting or retreating the exciter filter 22 into or from the optical path, a barrier filter operating button for inserting or retreating the barrier filter 24 into or from the optical path, and a both-filter operating button for inserting or retreating both the exciter filter 22 and the barrier filter 24 into or from the optical path. The barrier filter 24 may also include operating buttons for separately inserting or retreating the heat prevention filter 30, the light reducing filter 31, and the light shielding filter 32 into or from the optical path, an operating button for switching between the total reflection mirror/dichroic mirror 25.

The slit lamp 2 further includes a power source device 46 and drive devices 47 to 51. The power source device 46 supplies power to the light source 21 of the illumination optical system 2A. The drive device 47 causes the exciter filter 22 to insert into or retreat from the optical path of the illumination light. The drive device 48 causes the heat prevention filter 30 to insert into or retreat from the optical path of the illumination light. The drive device 49 causes the light reducing filter 31 to insert into or retreat from the optical path of the illumination light. The drive device 50 (light shielding drive means in the present invention) causes the light shielding filter 32 to insert into or retreat from the optical path of the illumination light. The drive device 51 drives the pair of slit blades of the slit forming means 33 to change the slit width. The slit lamp 2 further includes a drive device 52 for inserting or retreating the barrier filter 24 of the photographing optical system 2B (observation optical system 2C) into or from the optical path of the photographing light (observation light). Note that, the slit lamp 2 also includes various control devices which are not shown, such as a power source device for supplying power to the stroboscopic light source 28 and a drive device for driving the variable lens system 35L in the optical path direction.

The drive devices 47, 48, 49, 50, and 52 for filter insertion and retreat is composed of, for example, a solenoid etc. The drive device 51 for slit width change is composed of, for example, a motor etc. Note that, the drive device 51 may have a mechanism in which the slit width is manually changed by the knob operation etc. of the examiner, instead of such an electrical structure.

The slit lamp 2 further includes a control portion 44 for controlling the operations of the respective parts of the slit lamp 2, and a transmitting and receiving interface (I/F) 45 for transmitting and receiving various data to or from the computer 6. The control portion 44 is a control means in the present invention, which is composed of an arithmetic and control unit etc. such as a CPU. The control portion 44 includes a memory device (not shown) for storing operating states of the respective parts of the slit lamp 2 (for example, whether or not each of the filters is inserted into/retreated from the optical path). The control portion 44 controls the operation of the slit lamp 2 based on the operating states of the respective parts thereof, operating information inputted by the examiner, and the like. The transmitting and receiving I/F 45 is composed of a communication I/F circuit and the like.

(Control System of Computer)

Subsequently, a structure of a control system of the computer 6 will be described. The computer 6 includes a control portion 60, an image recording portion 61, an image converting portion 62, a timer 63, a display control portion 64, a transmitting and receiving I/F 65, an operating portion 66, and a program storing portion 67.

The control portion 60 composes the control means in the present invention together with the control portion 44 of the slit lamp 2. The control portion 60 is composed of an arithmetic and control unit such as a CPU. The control portion 60 executes a control program 68 stored in the program storing portion 67 to control various operations as described later. The control portion 60 includes a memory device for storing operating states of the respective parts of the eye fundus photographing system 1 (for example, whether or not each of the filters is inserted into/retreated from the optical path). The control portion 60 controls the operation of the eye fundus photographing system 1 based on the operating states, operating information inputted by the examiner, and the like.

Here, the program storing portion 67 is composed of a nonvolatile storage device such as a hard disk drive or a ROM. The control program 68 is installed in advance in the computer 6 and stored in the program storing portion 67.

The image recording portion 61 stores the right and left photographed images and is composed of a drive device for driving an image recording memory (image memory), a hard disk drive, a DVD-RAM, or the like. A recording mode of the photographed image in the image recording portion 61, and the like will be described in detail later. Note that, a combination of the right and left photographed images is recorded as a composite signal described later in the image recording portion 61. The image recording portion 61 composes an image recording means in the present invention.

The image converting portion 62 is composed of an arithmetic and control unit operated based on the control program 68, such as a CPU. The image converting portion 62 converts a monochrome photographed image sent from the left TV monitor 5L into a G signal of RGB signals and converts a monochrome photographed image sent from the right TV monitor 5R into an R signal thereof. In addition, the image converting portion 62 converts the G signal and the R signal into a composite signal. The composite signal is generally a normal video signal including RGB intensity data, RGB color data, and synchronization data of each frame. Here, the composite signal is a signal formed by a combination of both intensity data and the like of a G signal and intensity data of an R signal in each frame. The composite signal is recorded in the image recording portion 61 by the control portion 60. The image converting portion 62 is controlled by the control portion 60 to execute only processing for respectively converting the left and right photographed images into the G signal and the R signal or to execute up to conversion processing into the composite signal. The image converting portion 62 composes a conversion means in the present invention.

The timer 63 composes a time measuring means in the present invention and starts to measure a time under the control of the control portion 60. The control portion 60 monitors a time measured by the timer 63 and executes operating control described later. A stop timing of the time measurement of the timer 63 and a reset timing thereof are also controlled by the control portion 63.

The display control portion 64 selectively executes the following processings based on instructions from the control portion 60 in order to produce a three-dimensional image based on the right and left photographed images. According to a first processing mode of the display control portion 64, the G signal and the R signal of each frame which are converting by the image converting portion 62 are outputted to the three-dimensional image display monitor 7 in frame order (photographing order, that is, time-series order). According to a second-processing mode, the display control portion 64 outputs the composite signal of each frame which is recorded in the image recording portion 61 to the three-dimensional image display monitor 7 in frame order. The display control portion 64 composes a display control means in the present invention.

The transmitting and receiving I/F 65 is composed of a communication I/F circuit for transmitting and receiving various data to or from the slit lamp 2, the video timer 4, the TV monitors 5L and 5R, and the like.

The operating portion 66 is composed of an input device such as a keyboard, a pointing device such as a mouse or a trackball, or the like which is connected with the control portion 60. A control panel dedicated for the system 1 which is connected with the computer 6 can be also used as the operating portion 66. Photographing mode selecting operation may be performed by the operating portion 66 of the computer 6. For example, a predetermined photographing mode selecting screen is displayed on a monitor device (not shown) of the computer 6. Therefore, a check mark can be inputted to a check box of a desirable photographing mode by the operation of a mouse *or the like to perform the photographing mode selecting setting.

[operating Mode of Eye Fundus Photographing System]

Examples of operating aspects of the eye fundus photographing system 1 having the above-mentioned structure according to this embodiment will be described in detail based on eye fundus photographing work flows using this system.

Figure 4:
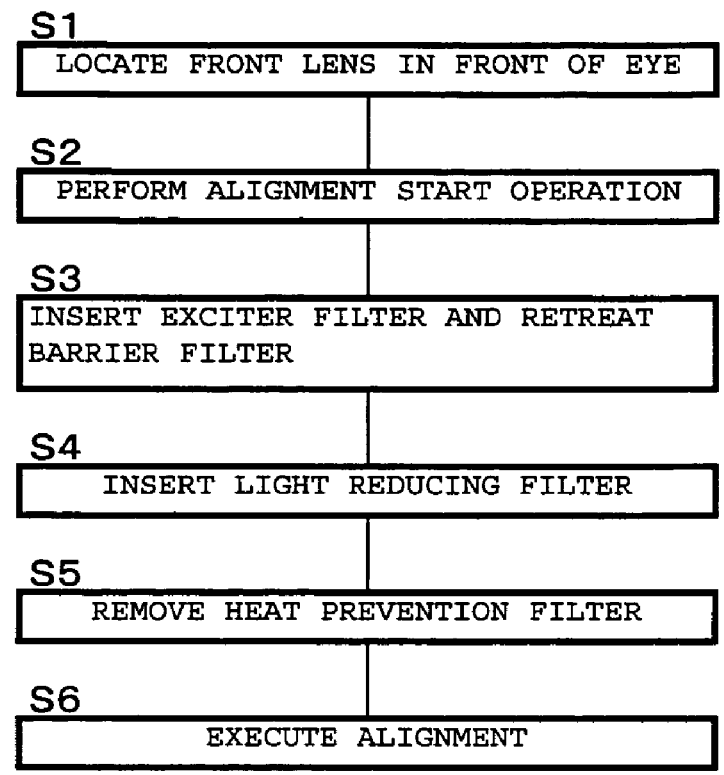
FIG. 4 is a flow chart showing an example of a control mode executed by the eye fundus photographing system according to the embodiment of the present invention.
Figure 5:
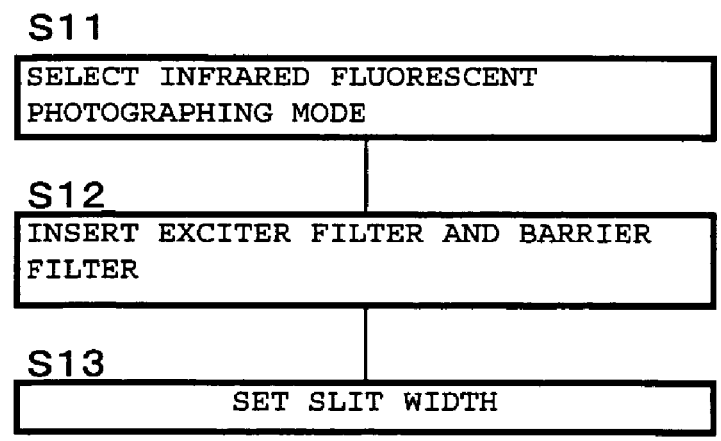
FIG. 5 is a flow chart showing an example of a control mode executed by the eye fundus photographing system according to the embodiment of the present invention.
Figure 6:
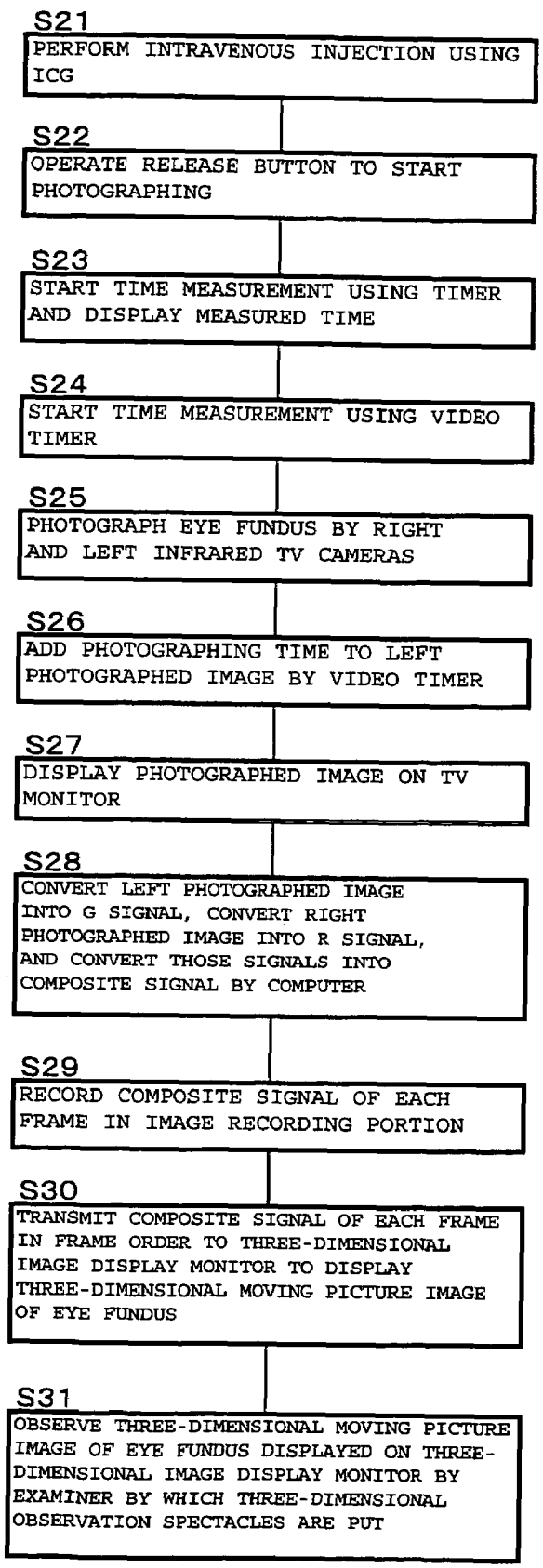
FIG. 6 is a flow chart showing an example of a control mode executed by the eye fundus photographing system according to the embodiment of the present invention.

Hereinafter, the operating aspects will be described with reference to flow charts shown in FIGS. 4 to 6. FIG. 4 shows alignment processing of the slit lamp 2 with the eye to be examined E. FIG. 5 shows an operating aspect when an infrared fluorescent photographing mode is selected as the photographing mode of the slit lamp 2. FIG. 6 shows an operating aspect for photographing processing of the fundus Er.

[Alignment of Slit Lamp; FIG. 4]

Before the eye fundus photographing is actually performed by the system 1, the alignment of the slit lamp 2 with the eye to be examined E is performed in the same manner as the conventional manner. In the alignment of the slit lamp 2, in order to prevent the pupil of the eye to be examined E from constricting, alignment light having an infrared wavelength region is used as in the case of a nonmydriatic type fundus camera. Here, it is general that a small amount of ICG is injected to a person to be examined by an intravenous injection and the alignment is performed using light produced from the ICG as background light.

First, the front lens 9 is located in front of the eye to be examined E (Step S1). In this embodiment, a contact lens is used as the front lens 9, so the front lens 9 is located in contact with the cornea of the eye to be examined E. At this time, the examiner may hold the front lens 9 in his/her hand. When a front lens holder is available, the front lens 9 may be held thereby.

For example, the alignment starts in response to the operation of an alignment start button (not shown) provided in the slit lamp 2 or the computer 6 (Step S2). When the alignment start operation is performed, the exciter filter 22 is inserted into the optical path and the barrier filter 24 is retreated from the optical path (Step S3). Note that, the exciter filter operating button and the barrier filter operating button may be operated to set filter positions.

When the exciter filter 22 is inserted into the optical path and the barrier filter 24 is retreated from the optical path, the control portion 44 of the slit lamp 2 transmits a control signal to the drive device 49 according to the operating states of the those filters. Therefore, the operation of the drive device 49 is controlled to insert the light reducing filter 31 into the optical path (Step S4). Note that, the control processing of the light reducing filter 31 may be executed by the control portion 60 of the computer 6. According to such control processing, a clear image obtained with a preferable exposure state using the light reducing filter 31 can be displayed on the TV monitor 5L or the like during alignment-which requires high accuracy. Thus, it is possible to perform the alignment of the slit lamp 2 with high accuracy.

When the heat prevention filter 30 for cutting off the light of infrared wavelength region is located on the optical path, the control portion 44 transmits a control signal to the drive device 48 in response to the insertion of the exciter filter 22 into the optical path. Therefore, the drive device 48 is controlled to retreat the heat prevention filter 30 from the optical path (Step S5). When the heat prevention filter 30 is retreated from the optical path, a retreat state thereof is maintained. According to such a control processing, the heat prevention filter 30 is automatically retreated from the optical path in accordance with the use of the exciter filter 22, so operability is improved. In addition, it is possible to prevent a state in which the retreat operation of the heat prevention filter 30 is forgotten to interrupt photographing, so the photographing can be smoothly performed.

When the light shielding filter 32 is located on the optical path, the control portion 44 transmits the control signal to the drive device 50 to retreat the light shielding filter 32 from the optical path.

After the positions of the filters are set as described above, the alignment of the slit lamp 2 with the eye to be examined E is executed (Step S6). The alignment is executed as in a conventional case. The examiner may manually perform the alignment while observing the eye fundus images displayed on the TV monitors 5L and 5R or the slit lamp 2 may be automatically perform the alignment.

[Infrared fluorescent Photographing]

(Photographing Mode Selection; FIG. 5)

The examiner operates the photographing mode selecting portion 43 (or the operating portion 66) to perform the photographing mode selection. Hereinafter, the case where the infrared fluorescent photographing mode is selected will be described. When there are a plurality of infrared fluorescent photographing modes, for example, when there are an infrared fluorescent photographing mode for three-dimensional moving picture and a normal infrared fluorescent photographing mode, it is assumed to select the infrared fluorescent photographing mode for three-dimensional moving picture. For example, even when another photographing mode such as a normal slit lamp photographing (observation) mode is shifted to the infrared fluorescent photographing mode, the eye fundus photographing system 1 performs the same operation. Hereinafter, a control aspect in the case where the infrared fluorescent photographing mode is selected will be described with reference to the flow chart shown in FIG. 5. Note that, the mode selection may be performed before the alignment processing.

When the infrared fluorescent photographing mode is selected by the photographing mode selecting portion 43 (Step S11), the control portion 44 of the slit lamp 2 transmits control signals to the drive devices 47 and 52 based on a signal sent from the photographing mode selecting portion 43. Therefore, the drive device 47 is controlled to insert the exciter filter 22 into the optical path and the drive device 52 is controlled to insert the barrier filter 24 into the optical path (Step S12). Thus, the exciter filter 22 and the barrier filter 24 are automatically located on the optical path by only the selective operation of the infrared fluorescent photographing mode, so the operability at the time of starting the infrared fluorescent photographing is improved.

In the case where the heat prevention filter 30 is located on the optical path, such as the case of shifting from another photographing (observation) mode, the control portion 44 controls the drive device 48 to retreat the heat prevention filter 30 from the optical path in response to the insertion of the exciter filter 22 into the optical path. Therefore, the improved operability and the smooth photographing are attempted as in the case of the alignment.

When the light shielding filter 32 is located on the optical path, the control portion 44 transmits a control signal to the drive device 50 to retreat the light shielding filter 32 from the optical path.

The control portion 44 transmits a control signal to the drive device 51 in response to the location of the exciter filter 22 on the optical path to maximize the slit width formed by the slit forming means 33 (Step S13). Therefore, the eye to be examined E is irradiated with the illumination light without any illumination light being blocked, so a large amount of light can be obtained. As described above, in order to prevent interference between the illumination light and the photographing light, a slit width for blocking a part of the illumination light may be set. Even in this case, it is possible to apply a slit width sufficiently larger than a slit width used for observation using a normal slit lamp.

The control portion 44 may control to selectively locate the total reflection mirror 25 for totally reflecting the light having the infrared wavelength region on the optical path in response to the selection setting of the infrared fluorescent photographing mode, thereby obtaining a bright photographed image. When the eye fundus photographing using the photographing optical system 2B and the eye fundus photographing using the observation optical system 2C are simultaneously performed, the control is performed to locate the dichroic mirror 25 on the optical path.

(Photographing processing; FIG. 6)

Next, infrared fluorescent photographing processing of the fundus Er that follows the above-mentioned photographing mode selection processing will be described with reference to the flow chart shown in FIG. 6.

Hereinafter, assume that the front lens 9 is located in front of the eye to be examined E and the fundus Er is illuminated with the illumination light from the light source 21. Here, the illumination light from the light source 21 is condensed by the condensing lenses 27 and 29. Light having a predetermined wavelength region (about 780 nm) is extracted from the illumination light by the exciter filter 22. The fundus Er of the eye to be examined E is irradiated with the extracted light passing through the condensing lens 34, the prism P, and the front lens 9.

The control portion 44 transmits a control signal to the computer 6 through the transmitting and receiving I/F 45 simultaneously with the turning on of the light source 21. The control portion 60 of the computer 6 causes the timer 63 to start time measurement in response to the received control signal. The control portion 60 monitors a time measured by the timer 63 and transmits a control signal to the slit lamp 2 based on the control program 68 or in response to the lapse of time set in advance by the examiner. The control portion 44 of the slit lamp 2 stops the irradiation of the illumination light to the eye to be examined E based on the control signal. The irradiation stop method includes a method of controlling the drive device 50 to insert the light shielding filter 32 into the optical path and a method of controlling the power source device 46 to stop the power supply to the light source 21. The set time is determined based on an amount of the illumination light per unit time, an allowable amount of the irradiation light for the eye to be examined E, or the like. A purpose of such control processing is to limit an amount of the integration light of the illumination light with which the eye to be examined E is irradiated, that is, an amount of the integration heat to an allowable value or less. Therefore, the safety of photographing is ensured. It is preferable to execute the control processing every time the light source 21 is turned on.

In the photographing processing, first, the person to be examined is subjected to the intravenous injection of the ICG 100 as an infrared fluorescent dye material by the examiner (Step S21). Then, the examiner operates the release button 42 to instruct the start of photographing (Step S22). Note that, the release button 42 may be operated immediately before the intravenous injection of the ICG 100.

The control portion 44 of the slit lamp 2 controls the timer 41 to start time measurement in response to a signal from the release button 42. A time measured by the timer 41 is displayed on a display portion (not shown) of the slit lamp 2, the TV monitor 5L, or the like, so that the displayed time is used in order that the examiner recognizes a photographing time (Step S23).

The control portion 44 transmits a control signal to the computer 6 through the transmitting and receiving I/F 45 in response to the received signal from the release button 42. The control portion 60 of the computer 6 detects the start of photographing based on the control signal and transmits a control signal to the video timer 4. The video timer 4 starts time measurement in response to the control signal from the computer 6.

Eye fundus reflection light of the illumination light with which the fundus Er of the eye to be examined E is irradiated is taken out to obtain the left and right photographing light beams by the left and right objective lenses 23L and 23R through the front lens 9 and the prism P. The magnifications of the left and right photographing light beams are changed by the variable lens systems 35L and 35R. Light beams each having a predetermined infrared wavelength region are extracted from the left and right photographing light beams by the barrier filter 24 and respectively condensed by the condensing lenses 36L and 36R. The condensed light beams are totally reflected on the total reflection mirror 25 and guided to the infrared TV cameras 3L and 3R respectively by the TV relay lens system including the condensing lens 37L and the reflecting mirror 38L and the TV relay lens system including the condensing lens 37R and the reflecting mirror 38R. The infrared TV cameras 3L and 3R respectively receive the left and right photographing light beams to photograph an image of the fundus Er at a predetermined frame rate (Step S25). At this time, photographing timings of the respective frames obtained by both the infrared TV cameras 3L and 3R are synchronized based on the synchronization signal sent through the synchronous cable C.

The photographed image (video signal) obtained by the left infrared TV camera 3L is transmitted to the video timer 4 and the photographing time is added to the photographed image (Step S26). The photographed image to which the photographing time is added is displayed as a monochrome moving picture image on the TV monitor 5L (Step S27). On the other hand, the photographed image obtained by the right infrared TV camera 3R is transmitted to the TV monitor 5L and displayed as a monochrome moving picture image (Step S27). The respective TV monitors 5L and 5R sequentially transmit the monochrome photographed images to the computer 6.

The computer 6 performs the following processing on the photographed images transmitted from the left and right TV monitors 5L and 5R. First, the control portion 60 sends the monochrome photographed images sequentially transmitted from the TV monitors 5L and 5R to the image converting portion 62. The image converting portion 62 converts the monochrome photographed image of each frame which is sent from the left TV monitor 5L into the G signal of the RGB signals and converts the monochrome photographed image of each frame which is sent from the right TV monitor 5R into the R signal thereof. In addition, the image converting portion 62 converts the G signal and the R signal into the composite signal of each frame (Step S28). The composite signal of the photographed image of each frame which is produced by the image converting portion 62 is recorded in the image recording portion 61 by the control portion 60 (Step S29).

A synthesized image based on the composite signal is an image reflecting a parallax based on a separate distance between the left and right objective lenses 23L and 23R, that is, a displacement between the light receiving positions of the photographing light beams on light receiving surfaces of the left and right infrared TV cameras 3L and 3R. Therefore, the synthesized image is a three-dimensional image in which the left photographed image derived from the G signal and the right photographed image derived from the R signal are shifted from each other in a right-and-left direction.

Next, the display control portion 64 sequentially reads out the composite signals of the photographed images of the respective frames from the image recording portion 61 in photographing frame order and sequentially transmits the composite signals to the three-dimensional image display monitor 7 through the transmitting and receiving I/F 65 (Step S30). Therefore, a three-dimensional moving picture image of the fundus Er is displayed on the three-dimensional image display monitor 7. Such processing of the display control means 64 may be automatically executed in succession to the record processing of Step S29 or executed in response to a request inputted from the operating portion 66 or the like by, for example, the examiner.

The examiner or the like puts on the three-dimensional observation spectacles 8 and views the three-dimensional image displayed on the three-dimensional image display monitor 7. Therefore, the examiner observes the three-dimensional moving picture image of the fundus Er which is obtained by the infrared fluorescent photographing (Step S31).

At this time, the longitudinal magnification is increased by the front lens 9, so the spacial effect of the observed three-dimensional image is increased. Therefore, it is possible to clearly recognize not only a state of a retinal blood vessel but also a state of a choroidal blood vessel located thereunder.

Note that the photographed image can be three-dimensionally displayed by the computer 6 in real time. For example, the left and right photographed images sent from the left and right TV monitors 5L and 5R at a predetermined frame rate are successively converted into the RGB signals by the image converting portion 62 and the RGB signals are transmitted to the three-dimensional image display monitor 7 by the display control portion 64 in frame order. Therefore, the three-dimensional image can be displayed in real time. At this time, the left and right photographed images converted into the RGB signals may be further converted into the composite signal by the image converting portion 62 and the composite signal may be recorded in the image recording portion 61.

[Operation and Effect]

The operation and the effect which are produced by the eye fundus photographing system 1 according to this embodiment as described above will be described.

First, according to the eye fundus photographing system 1, as described above, the three-dimensional moving picture image can be obtained in the infrared fluorescent photographing of the eye fundus. In addition, a plurality of doctors and the like, putting on the three-dimensional observation spectacles 8 can simultaneously observe the three-dimensional moving picture image, so this is effective when the diagnosis is made by a plurality of persons. Further, the three-dimensional image can be observed in real time.

According to the eye fundus photographing system 1, as compared with the three-dimensional image produced by the parallel shift method in the fundus camera, the right and left photographing light beams are simultaneously obtained and the right and left photographed images based on the right and left photographing light beams are synthesized with each other to produce the three-dimensional image. Therefore, the three-dimensional image obtained by the eye fundus photographing system 1 is produced from two images obtained by simultaneous photographing, so such a three-dimensional image becomes an accurate image.

The front lens 9 for increasing the longitudinal magnification is located in front of the eye to be examined E, so a suitable three-dimensional moving picture image having an increased spacial effect is obtained. Therefore, it is possible to clearly recognize a positional relationship between a new blood vessel and a lesion portion on the fundus Er in a depth direction. In particular, it is possible to clearly grasp a three-dimensional positional relationship between a retinal blood vessel and a choroidal blood vessel. This is effective for photocoagulation treatment described later.

The computer 6 causes the image recording portion 61 to record a combination of the right and left photographed images as the composite signal derived from the G signal and the R signal. Therefore, the three-dimensional moving picture image can be observed using a general TV monitor which can be applied to the composite signal, so versatility is high.

The photographing time is displayed with the three-dimensional moving picture image. Therefore, the lapse of time from the start of photographing can be grasped, so it is possible to support the diagnosis made by a doctor. In addition, the measurement of the photographing time automatically starts in response to the photographing started by the operation of the release button 42, so an accurate photographing time can be obtained.

The TV monitors 5L and 5R for respectively displaying the left and right photographed images are provided. This is effective, for example, when the left and right photographed images are separately to be observed.

The structure for infrared fluorescent photographing of the eye fundus according to the present invention can be added to a normal slit lamp, so it is possible to realize space-saving in a doctor's office or an examination room. In actual medical fields, there is also the case where the infrared fluorescent photographing is performed in succession to the examination using the normal slit lamp. In such a case, an examination process can be smoothly shifted, so that a burden on the person to be examined can be reduced. In particular, the alignment is performed in the previous examination, so it is unnecessary to perform alignment again before the infrared fluorescent photographing. Such a point may be advantage.

When the structure of the present invention is added to a slit lamp connected with a photocoagulator, processing can be promptly shifted to photocoagulation treatment after the lesion portion of a blood vessel on the fundus Er of the eye to be examined is grasped in detail by the infrared fluorescent photographing. Unlike conventional photocoagulation treatment with reference to a still image of the eye fundus, the photocoagulation treatment can be conducted while the three-dimensional moving picture image of the eye fundus is observed in real time. In this case, the spacial effect is increased by the front lens 9, so the state of the eye fundus blood vessel can be grasped in detail. Therefore, it is possible to easily perform high accuracy photocoagulation.

When the retinal blood vessel exists above the choroidal blood vessel which becomes a laser irradiation target, the slit lamp 2 is swung to change a laser irradiation angle to the fundus Er. Therefore, it is possible to perform laser treatment on the target choroidal blood vessel with avoiding the retinal blood vessel. Such a laser irradiation method is realized by clearly grasping the positional relationship between the retinal blood vessel and the choroidal blood vessel, which is made by the present invention.

When the laser treatment is performed using the system of the present invention, a laser oscillating device for oscillating laser light for photocoagulation treatment and light guiding means for guiding the oscillated laser light to the illumination optical system 2A, such as an optical fiber, are provided as in a normal case. The fundus Er is irradiated with the guided laser light along the optical axis of the illumination optical system 2A. The laser oscillating device and the light guiding means compose laser irradiation means in the present invention.

The total reflection mirror 25 for totally reflecting light beams each having the infrared wavelength region, of the right and left photographing light beams to guide the totally reflected light beams to the right and left photographing optical system 2B is used for the infrared fluorescent photographing. In this case, a bright photographed image can be obtained without a waste reduction in photographing light amount.

On the other hand, the dichroic mirror 25 for reflecting light beams each having the infrared wavelength region, of the right and left photographing light beams to guide the reflected light beams to the right and left photographing optical system 2B and transmitting light beams each having the visible wavelength region to guide the transmitted light beams to the right and left photographing optical system 2B is used. In this case, photographing can be performed during observation using the eyepieces 26L and 26R of the slit lamp 2, so that the convenience on examination is improved.

The exciter filter 22 and the barrier filter 24 are located on the optical path by only setting of the infrared fluorescent photographing mode selected by the photographing mode selecting portion 43. Therefore, photographing can be smoothly started because of high operability. In addition, for example, a fault in which the locations of those filters are forgotten is prevented.

When the exciter filter operating button is operated to locate the exciter filter 22 on the optical path, it is also possible that the control portion 44 control the drive device 52 to insert the batter filter 24 into the optical path. Even in such a structure, the operability at the time of starting the infrared fluorescent photographing is improved.

When the exciter filter 22 is inserted into the optical path, the heat prevention filter 30 for cutting off the infrared wavelength region is automatically retreated from the optical path, so an effort for retreating the heat prevention filter 30 from the optical path is unnecessary. Therefore, the operability is improved and there is no case where photographing is executed with a state in which the heat prevention filter 30 is located.

When the exciter filter 22 is located on the optical path and the barrier filter 24 is retreated from the optical path, that is, when the slit lamp 2 is to be aligned with the eye to be examined E, the light reducing filter 31 is automatically inserted into the optical path. Therefore, the alignment can be easily executed based on a clear image with an adequate exposure state.

When the exciter filter 22 is inserted into the optical path, the slit width is widened by the slit forming means 33. Therefore, an illumination light amount is automatically increased, so that a clear photographed image can be obtained. In particular, when the slit width is maximized to prevent the illumination light from being blocked, the illumination light amount can be used without wastage. When the slit width is adjusted to prevent the illumination light and the photographing light from overlapping with each other, it is possible to prevent the illumination light and the photographing light from interfering with each other. Thus, a preferable photographed image can be obtained.

When a predetermined set time elapses from the start of irradiation with the illumination light, the power supply to the light source 21 is stopped to interrupt the illumination or the light shielding filter 32 is inserted into the optical path. Therefore, the irradiation of the illumination light to the eye to be examined E is automatically stopped, so that it is possible to prevent damage to the eye to be examined E which is caused by over irradiation with the illumination light to maintain the safety during photographing.

Another mode of the three-dimensional image displayed on the three-dimensional image display monitor 7 maybe a three-dimensional image formed by synthesizing the left and right monochrome photographed images obtained by the infrared TV cameras 3L and 3R with each other. A three-dimensional viewer capable of observing the three-dimensional image with a naked eye state without using the three-dimensional observation spectacles 8 has been proposed, so the three-dimensional viewer can be also used as the three-dimensional image display monitor 7.

In the above-mentioned embodiment, the right and left photographed images are converted into the green signal of the RGB signals and the red signal thereof. The right and left photographed images may be converted into two different color signals of the RGB signals. That is, it is possible that one of the right and left photographed images be converted into the R signal and the other thereof be converted into a B (blue) signal. It is also possible that the one be converted into the G signal and the other be converted into the B signal. In such cases, a spectacles having right and left color plates corresponding to the converted colors is used as the three-dimensional observation spectacles 8. Here, assume that a "color signal" indicates each color signal of the RBG signals, that is, the R signal, the G signal, or the B signal.

The structure described in detail is just an example related to the embodiment of the present invention. Thus, various modifications can be naturally made without departing from the spirit of the present invention.

What is claimed is:

1. An eye fundus photographing system, comprising:
    an illumination optical system that includes a light source for emitting illumination light and an exciter filter for transmitting a specific wavelength region of the illumination light emitted from the light source and that emits the illumination light passing through the exciter filter to a fundus of an eye to be examined;
    a photographing optical system including right and left objective lenses for taking right and left photographing light beams based on infrared fluorescence radiated from an infrared fluorescent dye material excited by the illumination light emitted to the fundus and a barrier filter for transmitting a predetermined infrared wavelength region of each of the right and left photographing light beams;
    right and left photographing means for obtaining photographed images of respective frames based on the right and left photographing light beams passing through the barrier filter;
    synchronization means for synchronizing the respective frames between the right and left photographing means; and
    three-dimensional image displaying means for displaying a three-dimensional moving picture image based on the photographed images of the synchronized respective frames which are obtained by the right and left photographing means.

2. An eye fundus photographing system according to claim 1, further comprising a longitudinal magnification increasing lens for increasing longitudinal magnification of each of the photographed images obtained by the right and left photographing means.

3. An eye fundus photographing system according to claim 1, further comprising:
    converting means for converting the right and left photographed images of the respective frames which are obtained by the right and left photographing means into two different color signals of RGB signals; and
    display control means for outputting the converted two different color signals of each of the frames to the three-dimensional image displaying means in frame order to display the three-dimensional moving picture image.

4. An eye fundus photographing system according to claim 1, further comprising:
    converting means for converting the right and left photographed images of the respective frames which are obtained by the right and left photographing means into two different color signals of RGB signals and converting the two different color signals of the respective frames into a composite signal by synthesization;
    image recording means for recording the converted composite signal of each of the frames; and
    display control means for outputting the recorded composite signal of each of the frames to the three-dimensional image displaying means in frame order to display the three-dimensional moving picture image.

5. An eye fundus photographing system according to claim 1, wherein
    the synchronization means comprises:
    a synchronization signal generating circuit that is provided in one of the right and left photographing means and that generates a synchronization signal in synchronization with each of the frames of the one of the right and left photographing means;
    a cable for connecting between the right and left photographing means and transmitting the synchronization signal generated by the synchronization signal generating circuit to the other of the right and left photographing means; and
    a synchronous control circuit that is provided in the other of the right and left photographing means and that controls each of the frames of the other of the right and left photographing means in response to the synchronization signal transmitted through the cable.

6. An eye fundus photographing system according to claim 1, further comprising:
    time measuring means for staring time measurement in response to start of illumination of the fundus with the illumination light from the light source; and
    control means for stopping the illumination when a time measured by the time measuring means reaches a preset time.

7. An eye fundus photographing system according to claim 1, wherein
    the illumination optical system further comprises light shielding means for blocking the illumination light emitted from the light source, and the eye fundus photographing system further comprises:

light shielding drive means for inserting and retreating the light shielding means into and from an optical path of the illumination optical system;

time measuring means for staring time measurement in response to start of illumination of the fundus with the illumination light from the light source; and control means for controlling the light shielding drive means to insert the light shielding means into the optical path when a time measured by the time measuring means reaches a preset time.

8. An eye fundus photographing system according to claim 1, wherein the illumination optical system further comprises an observation light source for emitting illumination light for fundus observation, and the eye fundus photographing system further comprises:

an observation optical system that uses the right and left objective lenses common to the photographing optical system and respectively guides right and left observation light beams extracted from fundus reflection light of the illumination light for fundus observation to right and left eyepieces by the right and left objective lenses; and optical path changing means for guiding the right and left photographing light beams taken by the right and left objective lenses to optical paths of the photographing optical system and guiding the right and left observation light beams to optical paths of the observation optical system.

9. An eye fundus photographing system according to claim 8, wherein the optical path changing means comprises a total reflection mirror for totally reflecting light having an infrared wavelength region, of each of the right and left photographing light beams passing through the barrier filter to guide the totally reflected light to an optical path of the photographing optical system.

10. An eye fundus photographing system according to claim 8, wherein the optical path changing means comprises a dichroic mirror for reflecting light having an infrared wavelength region, of each of the right and left photographing light beams passing through the barrier filter to guide the reflected light to the optical path of the photographing optical system and transmitting light having a visible wavelength region to guide the transmitted light to the optical path of the observation optical system.

11. An eye fundus photographing system according to claim 8, further comprising laser irradiating means for irradiating the fundus with laser light for photocoagulation treatment along an optical axis of the illumination optical system.

* * * * *